United States Patent [19]

Mieno et al.

[11] Patent Number: 4,719,895

[45] Date of Patent: Jan. 19, 1988

[54] METHOD FOR CONTROLLING AN OXYGEN CONCENTRATION SENSOR

[75] Inventors: Toshiyuki Mieno; Toyohei Nakajima; Yasushi Okada; Nobuyuki Oono, all of Wako, Japan

[73] Assignee: Honda Giken Kogyo Kabushiki Kaisha, Tokyo, Japan

[21] Appl. No.: 946,402

[22] Filed: Dec. 23, 1986

[30] Foreign Application Priority Data

Dec. 26, 1985 [JP] Japan ............................. 60-294407

[51] Int. Cl.$^4$ ............................................ F02M 23/00
[52] U.S. Cl. ........................................ 123/589; 60/276
[58] Field of Search ................. 60/276; 123/440, 489, 123/589

[56] References Cited

U.S. PATENT DOCUMENTS

4,485,786 12/1984 Kashimura ................. 123/589 X
4,543,176 9/1985 Harada et al. .............. 123/489 X
4,611,562 9/1986 Nakano et al. ................. 123/440

Primary Examiner—Stephen F. Husar
Attorney, Agent, or Firm—Pollock, VandeSande & Priddy

[57] ABSTRACT

A method for controlling an oxygen concentration sensor mounted on an engine, including oxygen ion conductive solid electrolyte members operative as an oxygen pump element and a sensor cell element respectively, a source of pump current to be supplied to the oxygen pump element, and a heater element for heating the oxygen pump element and the sensor cell element. The method includes an operation for detecting an engine temperature of a time immediately before the start of the supply of a drive current of the heater element, and a control operation for starting the supply of the pump current after an elapse of a time period determined in response to the engine temperature from the start of the supply of the drive current of the heater element.

1 Claim, 8 Drawing Figures

METHOD FOR CONTROLLING AN OXYGEN CONCENTRATION SENSOR

BACKGROUND OF THE INVENTION

1. Field of the Invention

The present invention relates to a method for controlling an oxygen concentration sensor, and more particularly to a method for controlling a sensor for sensing an oxygen concentration in an exhaust gas of an internal combustion engine.

2. Description of Background Information

In order to accelerate the purification of the exhaust gas and to improve the fuel economy of an internal combustion engine, a feedback type air/fuel ratio control system is generally used, in which oxygen concentration in the exhaust gas is detected and air/fuel ratio of the mixture supplied to the engine is controlled to a target air/fuel ratio by a feedback control operation in accordance with a result of the detection of the oxygen concentration.

As an oxygen concentration sensor for use in such an air/fuel ratio control system, there is a type which is capable of producing an output signal whose level is proportional to the oxygen concentration in the exhaust gas of the engine in a region in which the air/fuel ratio of the mixture is larger than a stoichiometric air/fuel ratio, and the detail of which is disclosed in Japanese patent application laid open No. 58-153155. This oxygen concentration sensor includes an oxygen concentration sensing unit having a general construction including a pair of flat solid electrolyte members having oxygen ion permeability. These oxygen ion conductive solid electrolyte members are placed in the exhaust gas of the engine, and electrodes are respectively provided on the front and back surfaces of both of the solid elctrolyte members. In other words, each pair of electrodes sandwich each solid electrolyte member. These two solid electrolyte members each haing a pair of electrodes are arranged in parallel so as to face each other and forming a gap portion, or in other words, a restricted region between them.

With this arrangement, one of the solid electrolyte members serves as an oxygen pump element and the other one of the solid electrolyte members serves as a sensor cell element for sensing an oxygen concentration ratio. In an ambient atmosphere of the exhaust gas, a drive current is supplied across the electrodes of the oxygen pump element in such a manner that the electrodes facing the gap portion operates as a negative electrode. By the supply of this current, i.e. a pump current, the oxygen component of the gas in the gap portion is ionized on the surface of the negative electrode of the oxygen pump element. The oxygen ions migrate through the inside of the oxygen pump element to the positive electrode, where the oxygen ions are released from the surface thereof in the form of the oxygen gas.

While this movement of the oxygen ions is taking place, the oxygen concentration becomes different for the gas in the gap portion and the gas outside the sensor cell element because of a decrease of the oxygen gas component in the gap portion. Therefore, a voltage develops across the electrodes of the sensor cell element. If the magnitude of the pump current supplied to the oxygen pump element is controlled so that the voltage generated across the sensor cell element is maintained constant, the magnitude of the pump current varies substantially in proportion to the oxygen concentration in the exhaust gas under a condition of a constant temperature. The pump current is then used as an output signal indicative of the oxygen concentration detection value.

By means of the magnitude of the pump current supplied to the oxygen pump element, a detection as to whether the air/fuel ratio of the mixture supplied to the engine is rich or lean is performed. In the case of the air/fuel ratio control system in which the air/fuel ratio is controlled by the supply of the air intake side secondary air, the secondary air is supplied when the air/fuel ratio is detected to be rich. On the other hand, the supply of the secondary air is stopped when the air/fuel ratio is detected to be lean. Thus the air/fuel ratio is controlled toward a target air/fuel ratio by the supply and stop of the air intake side secondary air.

In this type of oxygen concentration sensor, if an excessive current is supplied to the oxygen pump element, it causes the so called blackening phenomenon by which the oxygen ions are removed from the solid electrolyte members. For instance, when zirconium dioxide ($ZrO_2$) is used as the solid electrolyte, the oxygen ions $O_2$ are taken from the zirconium dioxide ($ZrO_2$) so that zirconium (Zr) is separated out. As a result of this blackening phenomenon, a deterioration of the oxygen pump element takes place rapidly, to cause a debasement of the operation of the oxygen concentration sensor as a whole.

Figure 1:
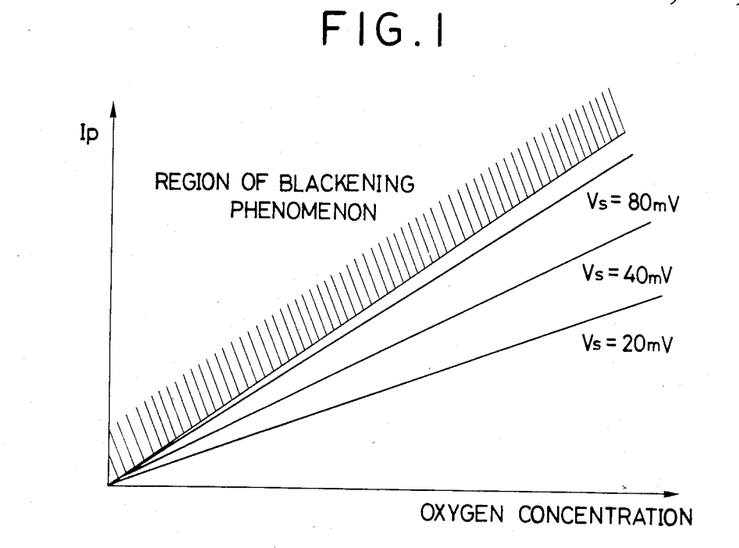
FIG. 1 is a diagram illustrating curves showing oxygen concentration versus pump current charateristic and a boundary of occurence of the blackening phenomenon.

FIG. 1 shows curves indicating a current $I_P$ to the oxygen pump element versus oxygen concentration relation and a boundary line of the occurence of the blackening phenomenon. As illustrated, magnitude of the current $I_P$ varies in proportion to the oxygen concentration, and the rate of variation is different for several different values of the voltage $V_s$ developing across the electrodes of the sensor cell element. In other words, the voltage Vs is a parameter which determines the relation between the magnitude of the current $I_P$ and the oxygen concentration. As illustrated in this figure, the boundary line of the occurence of the blackening phenomenon is shown, as in the case of the magnitude of the current $I_P$, as a first-degree function of the oxygen concentration value. Therefore, for preventing the blackening phenomenon, it is necessary that the magnitude of the supply current to the oxygen pump element is limited to be smaller than values in the region of the blackening phenomenon.

Further, in this type of the oxygen concentration sensor, it is necessary that the operating temperature of the sensing unit is sufficiently higher (for example, higher than 650° C.) than an exhaust gas temperature under a steady state operation, in order to obtain a proportional output signal characteristic in which the sensor output signal varies substantially in proportion to the oxygen concentration. To meet this requirement, a heater element which is made up of a heater wire, for example, is incorporated in the oxygen concentration sensing unit and a drive current is supplied to the heater element at the time of measurement so that heat is generated at the heater element.

When the supply of the heater current is started upon a cold start of the engine, the oxygen concentration sensing unit remains inactive because the temperature of the oxygen concentration sensing unit does not rise immediately to a level at which the desired proportional output signal characteristic is obtaned. On the other hand, after a hot start of the engine, the temperature of the oxygen concentration sensing unit reaches to the level at which the sensing unit is activated, within a relatively short time. Therefore, the detection of the activation of the oxygen concentration sensing unit can not be easily performed simply by using a time period elapsed after the start of the engine. Further, since the feedback control of the air/fuel ratio in response to the outout signal of the oxygen concentration sensor is enabled only after the completion of the activation of the oxygen concentration sensing unit, it is important to detect the activation of the oxygen concentration sensing unit accurately for the air/fuel ratio control operation. If the completion of activation of the oxygen concentration sensing unit is not detected accurately, the feedback control of the air/fuel ratio is not started at a proper time after the start of the engine, and an open loop control of the air/fuel ratio is performed before the start of the feedback control. Therefore, it has not been always possible to attain an optimum efficiency of the purification of the exhaust gas by means of conventional apparatuses.

SUMMARY OF THE INVENTION

An object of the present invention is therefore to provide a method for controlling an oxygen concentration sensor of an internal combustion engine with an air/fuel ratio control system, by which the completion of the activation of the oxygen concentration sensing unit is determined accurately, to start the feedback control of the air/fuel ratio.

According to the present invention, a method for controlling an oxygen concentration sensor mounted on an internal combustion engine having an exhaust gas passage, which sensor includes: a pair of oxygen ion conductive solid electrolyte members with electrodes and disposed in the exhaust gas passage; one of the oxygen ion conductive solid electrolyte members being operative as an oxygen pump element, and the other of the oxygen ion conductive solid electrolyte members being operative as a sensor cell element for measuring an oxygen concentration ratio; a pump current source for supplying a pump current to be supplied across the electrodes of the oxygen pump element; and a heater element arranged to heat the oxygen ion conductive solid electrolyte members when a heater current is supplied thereto, the method comprises: a detection step for detecting a temperature of the engine immediately before a start of a supply of the heater current; and a control step for controlling a supply of the pump current so that the supply of the pump current is started when an elapse of more than a time period determined correspondingly to the temperature of the engine from a time of the supply of the heater current, is detected.

In short, the method for controlling an oxygen concentration sensor is characterized in that the supply of the current to the electrodes of the oxygen pump element is started upon detection of an elapse of more than a time period corresponding to an engine temperature at a time of the start of the heater current, after the start of the supply of the drive current to the heater element.

DETAILED DESCRIPTION OF THE DRAWINGS

An embodiment of the method for controlling an oxygen concentration sensor of the present invention will be explained with reference to FIGS. 2 through 8 hereinafter.

Figure 2:
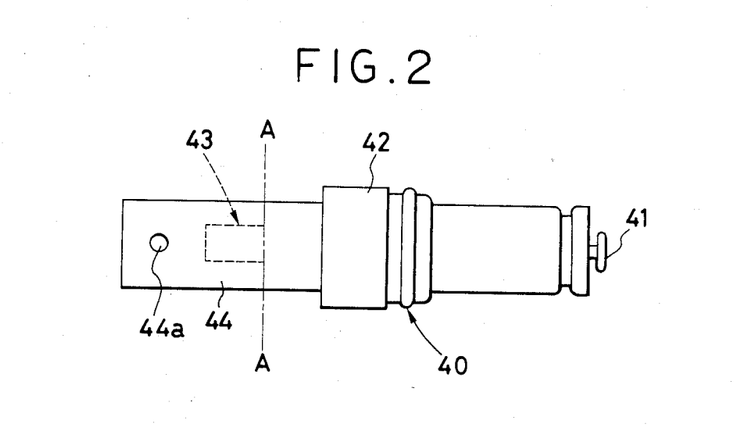
FIG. 2 is a side view of an oxygen concentration sensor which is suitable for application of the method according to the present invention.

As shown in FIG. 2, the oxygen concentration sensor generally denoted at 40 includes a housing 42 having a lead wire introducing hole 41 at an extremity thereof. At the other extremity of the housing 42, an oxygen concentration sensing unit 43 is mounted. The oxygen concentration sensing unit 43 is surrounded by a protection cover 44 which is formed into a cylinder and connected to the housing at an end portion thereof. The protection cover 44 is provided with a plurality of exhaust gas introduction holes 44a which are equally spaced on circumference. Four exhaust gas introduction holes 44a are provided in this example. In addition, a pair of the oxygen concentration sensor 40 illustrated on the left side of the line A—A of FIG. 2 is introduced into an exhaust manifold (not shown) when the sensor 40 is mounted for operation.

Figure 3:
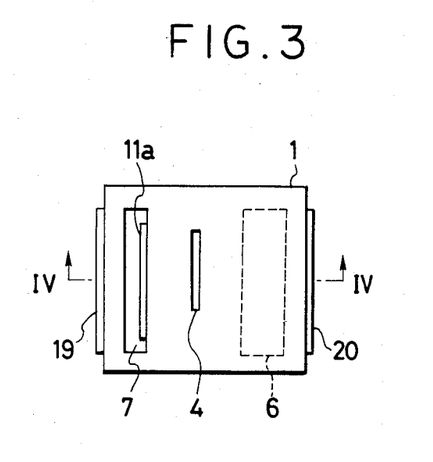
FIG. 3 is plan view of the oxygen concentration sensing unit provided in the sensor shown in FIG. 2.
Figure 4:
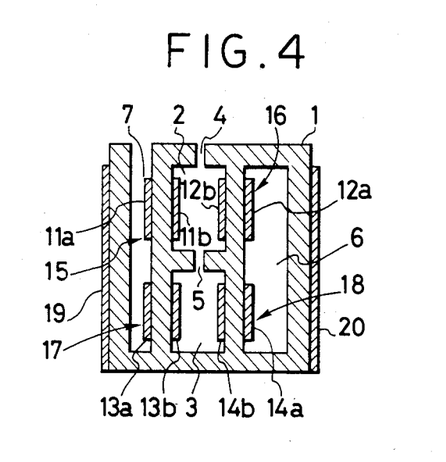
FIG. 4 is a sectional view of the oxygen concentration sensing unit taken along the line IV—IV of FIG. 3.

As shown in FIGS. 3 and 4, the oxygen concentration sensing unit 43 includes an oxygen ion conductive solid electrolyte member 1 having generally cubic configuration. In the oxygen ion conductive solid electrolyte member 1, first and second gas retaining chambers 2 and 3, which constitute gap portions, are provided. The first gas retaining chamber 2 leads to a gas introduction port 4 for introducing the measuring gas, i.e. the exhaust gas of the engine, from outside of the oxygen ion conductive solid electrolyte member 1. The gas introduction port 4 is positioned in an exhaust gas passage (not shown) of the internal combustion engine so that the exhaust gas can easily flow into the gas retaining chamber 2. In a wall between the first gas retaining chamber 2 and the second gas retaining chamber 3, there is provided a communication channel 5 so that the exhaust gas is introduced into the second gas retaining chamber 3 through the gas introduction port 4, the first gas retaining chamber 2 and the communication channel 5. Further, the oxygen-ion conductive solid electrolyte member 1 is provided with a reference gas chamber 6 into which outside air, for example, is introduced. The reference gas chamber 6 is provided in such a manner that it is separated from the first and second gas retaining chambers 2 and 3 by means of a partition wall between them. In a side wall of the first and second gas retaining chambers 2 and 3, on the opposite side of the reference gas chamber 6, there is provided an electrode protection cavity 7. The wall between the first gas retaining chamber 2 and the reference gas chamber 6 and the electrode protection cavity 7, there respectively are provided a pair of electrodes 12a and 12b, and a pair of electrodes 11a and 11b. The electrodes 11a, 11b, and 12a, 12b form a first set of electrodes associated with the first gas retaining chamber 2. Similarly, the wall between the second gas retaining chamber 3 and the gas reference chamber 6, and the wall between the second gas retaining chamber 3 and the electrode protection cavity 7 are respectively provided with a pair of electrodes 14a and 14b, and a pair of electrodes 13a and 13b. The electrodes 13a, 13b, and 14a, 14b form a second set of electrodes associated with the second gas retaining chamber 3. With this construction, the solid electrolyte member 1 and the pair of electrodes 11a and 11b together operate as a first oxygen pump unit 15. On the other hand, the solid electrolyte member 1 and the pair of electrodes 12a and 12b together operate as the first sensor cell unit 16. Similarly, the solid electrolyte member 1 and the pair of electrodes 13a and 13b together operate as a second oxygen pump unit 17, and the solid electrolyte member and the pair of electrodes 14a and 14b together operate as the second sensor cell unit 18. Further, heater elements 19 and 20 are respectively provided on an outer wall of the reference gas chamber 6 and an outer wall of the electrode protection cavity 7, respectively. The heater elements 19 and 20 are electrically connected in parallel with each other so as to heat the first and second oxygen pump units 15 and 17, and the first and second sensor cell units 16 and 18 equally. The heater elements 19 and 20 further have an effect to enhance the heat retaining property of the solid electrolyte member 1. The solid electrolyte member 1 is made up of a plurality of pieces, to form an integral member. In addition, the walls of the first and second gas retaining chambers 2 and 3 need not be made of the oxygen ion conductive solid electrolyte as a whole. At least portions of the wall on which the electrodes are provided must be made of the solid electrolyte.

As the oxygen ion conductive solid electrolyte, zirconium dioxide ($ZrO_2$) is suitably used, and platinum (Pt) is used as the electrodes 11a through 14b.

Figure 5:
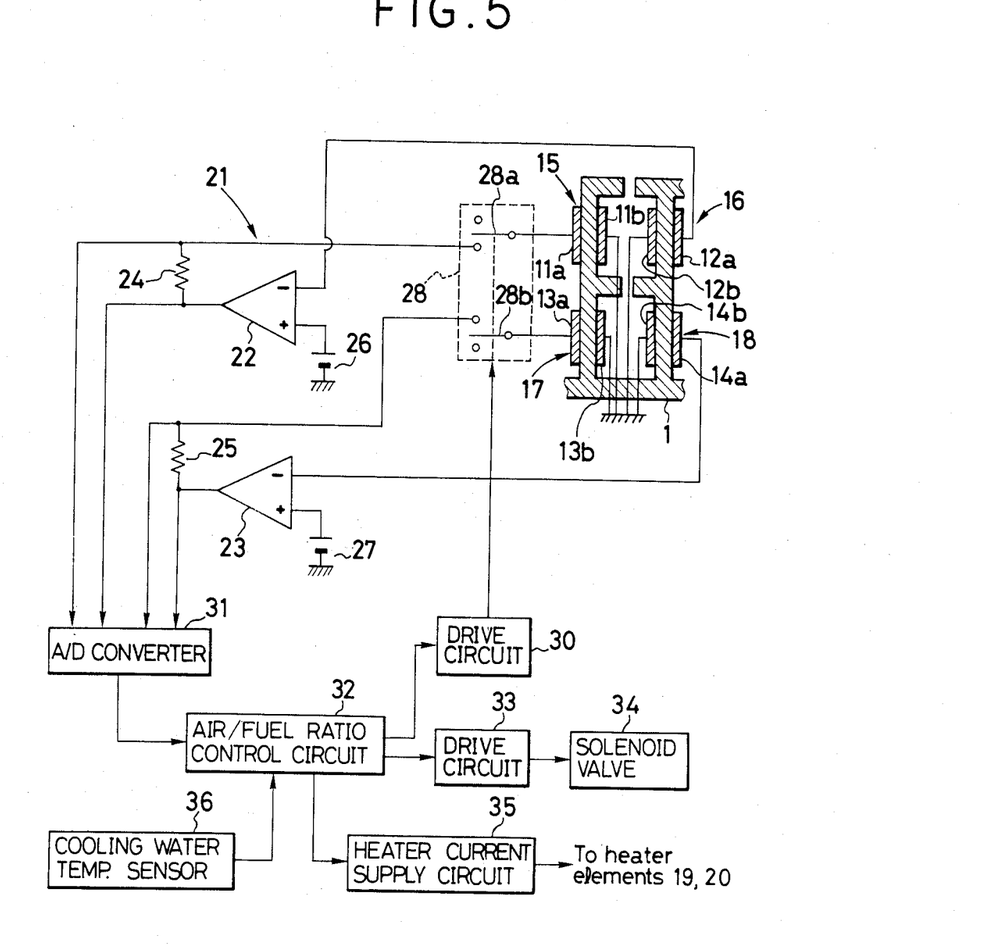
FIG. 5 is a circuit diagram showing a current supply circuit of the oxygen concentration sensor, in which the air/fuel ratio control system is also shown.

The first oxygen pump unit 15 and and the first sensor cell unit 16 form a first sensor, and the second oxygen pump unit 17 and the second sensor cell unit 18 form a second sensor. The first and second oxygen pump units 15 and 17, the first and second sensor cell units 16 and 18 are connected to a current supply circuit 21. As shown in FIG. 5, the current supply circuit 21 includes differential amplifiers 22 and 23, current detection resistors 24 and 25 for detecting the magnitude of the current, and sources of reference voltages 26 and 27, and a switch circuit 28. The electrode 11a provided on the outer surface of the first oxygen pump unit 15 is connected to an output terminal of the differential amplifier 22 through the current detection resistor 24 and a switch element 28a of the switch circuit 28. The electrode 11b provided on the inner surface of the first oxygen pump unit 15 is grounded. The electrode 12a provided on the outer surface of the first sensor cell unit 16 is connected to an inverting input terminal of the differential amplifier 22, and the electrode 12b on an inner surface of the first sensor cell unit 16 is grounded. Similarly, the electrode 13a provided on the outer surface of the second oxygen pump unit 17 is connected to an output terminal of the differential amplifier 23 through the current detection resistor 25, and a switch element 28b of the switch circuit 28. The electrode 13b provided on the inner surface of the second oxygen pump unit 17 is grounded. The electrode 14a provided on the outer surface of the second sensor cell unit 18 is connected to an inverting input terminal of the differential amplifier 23, and the electrode 14b provided on the inner surface of the sensor cell unit 18 is grounded. A non-inverting input terminal of the differential amplifier 22 is connected to the source of the reference voltage 26, and a non-inverting input terminal of the differential amplifier 23 is connected to the source of the reference voltage 27. Output voltages of the sources of the reference voltage 26 and 27 are set to a voltage (0.4 V for example) corresponding to the stoichiometric air/fuel ratio. With the circuit construction described above, the voltage appearing across the terminals of the current detection resistor 24 forms an output signal of the first sensor, and the voltage appearing across the terminals of the current detection resistor 25 forms an output signal of the second sensor. The voltages across the terminals of the current detection resistors 24 and 25 are supplied to the air/fuel ratio control circuit 32 through the A/D converter 31 having a differential input circuit. Thus, pump currents $I_P(1)$ and $I_P(2)$ flowing through the variable resistors 24 and 25 are read by the air/fuel ratio control circuit 32. The air/fuel ratio control circuit 32 comprises a microcomputer. An output signal of a cooling water temperature sensor 36 for sensing an engine cooling water temperature is connected to the air/fuel ratio control circuit 32. This air/fuel ratio control circuit 32 is further supplied with output signals of a plurality of sensors (not shown) for sensing operational parameters of the engine, such as an engine rotational speed, an absolute pressure in the intake pipe. Further, the solenoid valve 34 is connected to the air/fuel ratio control circuit 32 via the drive circuit 33. The solenoid valve 34 is provided in an air intake side secondary air supply passage (also not shown) leading to an intake manifold at a position downstream of a throttle valve of a carburettor of the engine. The air/fuel ratio control circuit 32 further controls the switching operation of the switch circuit 28, in such a manner that the drive circuit 30 drives the switch circuit 28 in accordance with a command from the air/fuel ratio control circuit 32. In addition, the differential circuits 22 and 23 are supplied with positive and negative power voltages.

On the other hand, the heater elements 19 and 20 are connected to a heater current supply circuit 35 which supplies currents to the heater elements 19 and 20 in response to a heater current supply start command from the air/fuel ratio control circuit 32. By the heater element 18 and 19 operated in this way, the oxygen pump units 15 and 17, and the sensor cell units 16 and 18 are heated to a suitable temperature level which is higher than the temperature of the exhaust gas.

With the thus constructed oxygen concentration sensor, the exhaust gas in an exhaust manifold flows into the first gas retaining chamber 2 through the gas introduction port 4 and is diffused therein. Also, the exhaust gas entered in the first gas retaining chamber 2 is introduced into the second gas retaining chamber 3 through the communication channel 5 and is diffused therein.

In the switch circuit 28, the switch elements 28a and 28b are normally positioned at intermediate positions as shown in FIG. 4, and driven to one of positions to select the first and the second sensors by the drive circuit 30. If the switch element 28a is positioned to connect the terminal 11a to the current detection resistor 24 and the switch element 28b is positioned to open the line connecting the electrode 13a and the current detection resistor 25, the switch circuit 28 is in the position for selecting the first sensor.

Under this condition for selecting the first sensor, the output signal level of the differential amplifier 22 is in a positive level when the air/fuel ratio of the mixture is in a lean range. This positive level output voltage is supplied to the series circuit of the first oxygen pump unit 15. Therefore, a pump current flows through the electrodes 11a and 11b of the first oxygen pump unit 15. Since this pump current flows from the electrode 11a to the electrode 11b, oxygen in the first gas retaining chamber 2 is ionized at the electrode 11b and moves through the oxygen pump unit 15 to the electrode 11a. At the electrode 11a, the oxygen is released in the form of oxygen gas. In this way, oxygen in the first gas retaining chamber 2 is pumped out.

By the pumping out of oxygen in the first gas retaining chamber 2, a difference in the oxygen concentration develops between the exhaust gas in the first gas retaining chamber 2 and a gas in the reference gas chamber 6. By this difference in the oxygen concentration, a voltage $V_s$ is generated across the electrodes 12a and 12b of the sensor cell unit 16, and in turn supplied to the inverting input terminal of the differential amplifier 22. Therefore, the voltage of the output signal of the differential amplifier 22 becomes proportional to the differential voltage between the voltage $V_s$ and a voltage $Vr_1$ of the output signal of the source of the reference voltage 26. Thus, the magnitude of the pump current becomes proportional to the oxygen concentration in the exhaust gas.

Figure 6:
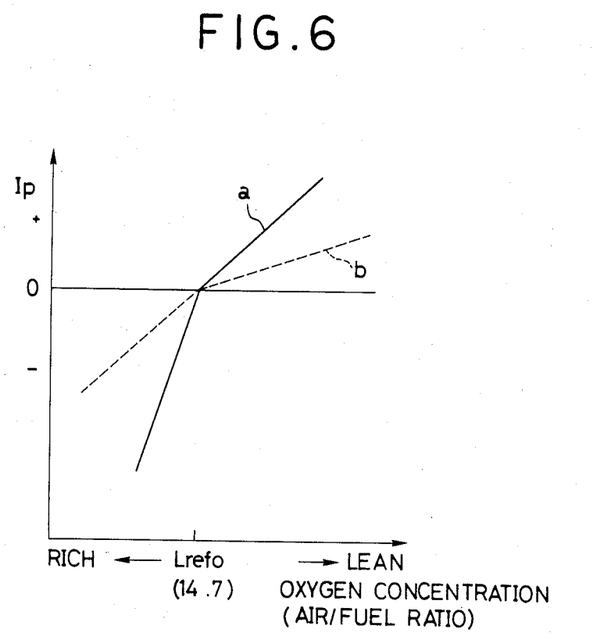
FIG. 6 is a diagram showing an output signal characteristic of the oxygen concentration sensor.

When the air/fuel ratio of the mixture is in a rich range, the voltage $V_s$ exceeds the output voltage $Vr_1$ of the source of the reference voltage 26. Therefore, the output signal level of the differential amplifier 22 turns from the positive level to the negative level. By this negative level, the pump current flowing across the electrodes 11a and 11b of the first oxygem pump unit 15 is reduced, and the direction of the flow of the current will be turned over. More specifically, the pump current will flow from the electrode 11b to the electrode 11a, so that the oxygen in the outside is ionized at the electrode 11a and in turn moves through the first oxygen pump unit 15 to the electrode 11b. At the electrode 11b, the oxygen is released in the form of oxygen gas into the first gas retaining chamber 2. In this way, the oxygen is pumped into the first gas retaining chamber 2. In summary, the operation of the apparatus is such that the pump current is supplied so that the oxygen concentration in the first gas retaining chamber 2 is maintained constant, and the oxygen is pumped in or out according to the direction of the pump current. Therefore, the magnitude of the pump current and the output signal voltage of the differential amplifier 22 become proportional to the oxygen concentration in the exhaust gas in both of the lean and rich ranges. In FIG. 6, the solid line shows the magnitude of the pump current $I_P$.

On the other hand, the pump current $I_P$ is expressed by the following equation:

$$I_P = 4e\sigma o(Poexh - Pov) \quad (1)$$

in which e represents the electric charge, $\sigma o$ represents the diffusion coefficient of the gas introduction port 4 against the exhaust gas, Poexh represents the oxygen concentration of the exhaust gas, and Pov represents the oxygen concentration in the first gas retaining chamber 2.

The diffusion coefficient $\sigma o$ can be expressed by the following equation:

$$\sigma o = D \cdot A / kTl \quad (2)$$

where A represents the sectional area of the gas introduction port 4, k represents boltzmann's constant, T represents absolute temperature, l represents the length of the gas introduction port 4, and D represents a diffusion constant.

On the other hand, the second sensor is selected when the switch element 28a is positioned to open the line connecting the electrode 11a and the current detection resistor 24, and the switch element 28b is positioned to connect the electrode 13a to the current detection resistor 25.

In this state of selecting the second sensor, the pump current is supplied across the electrodes 13a and 13b of the second oxygen pump unit 17 so that the oxygen concentration in the second gas retaining chamber 3 is maintained constant by an operation the same as that in the state where the first sensor is selected. Thus, the oxygen is pumped in or out by the pump current and the magnitude of the pump current and the output signal of the differential amplifier 23 vary in proportion to the oxygen concentration both in the lean range and in the rich range.

In the state in which the second sensor is selected, the magnitude of the pump current can be expressed by using the equation (1) with the diffusion coefficient $\sigma o$ calculated for the gas introduction port 4 and the communication channel 5 also, and the oxygen concentration in the second gas retaining chamber 3 as the value Pov.

On the other hand, it is known that the magnitude of the pump current becomes small as the increase in a diffusion resistance which is inversely proportional to the diffusion coefficient $\sigma o$, both in the lean range and the rich range of the air/fuel ratio. This means that, when the second sensor is selected, the diffusion resistance becomes larger than that in the state where the first sensor is selected. Therefore, as shown by the dashed line b in FIG. 6, the magnitude of the pump current is smaller than that in the state where the first sensor is selected, both in the lean range and in the rich range.

Further, by selecting suitable size and length of the communication channel 5, the characteristic curve of the pump current with the second sensor in the rich range connects straightly to the characteristic curve of the pump current with the first sensor in the lean range, at a point where $I_P$ is zero ($I_P = 0$). Thus, a characteristic curve of the pump current forming a straight line passing through the lean range and the rich range can be obtained by combining the first and second sensors. Also, with suitable control operation, characteristic curves of the output signals of the first and second differential amplifiers 22 and 23 can be connected straightly to each other at a point where the voltage level is equal to zero.

Figure 7:
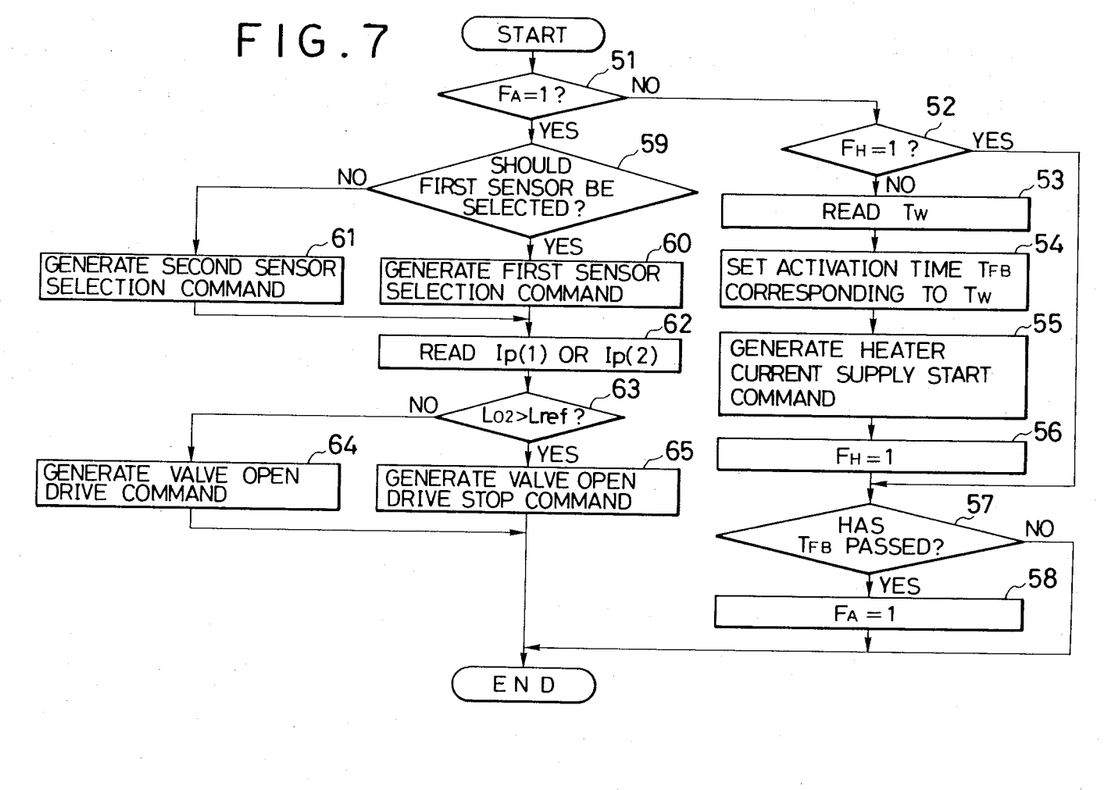
FIG. 7 is a flowchart showing steps of the control method according to the present invention.

The details of the control method according to the present invention will be explained with reference to the flowchart of FIG. 7 showing the operation of the air/fuel ratio control circuit 32 as follows.

Figure 8:
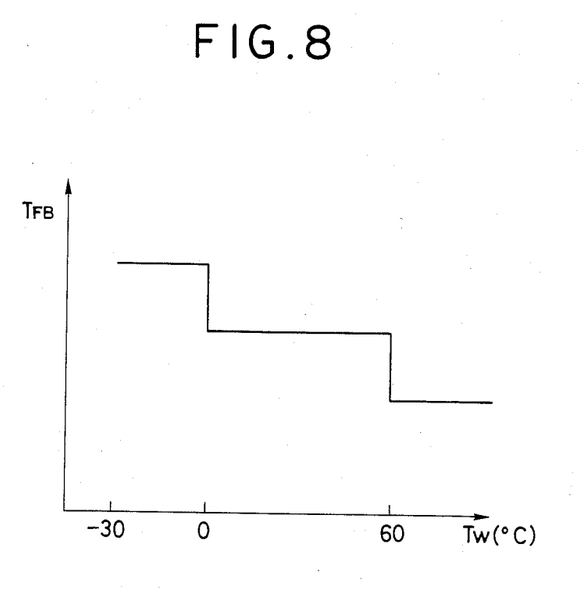
FIG. 8 is a diagram showing the relation between an activation time $T_{FB}$ and an engine cooling water temperature $T_W$.

The air/fuel ratio control circuit 32 sets "0"s, as initial values, for a flag $F_A$ for discriminating the completion of the activation of the sensor unit, and a flag $F_H$ for starting the supply of the heater current, upon closing of an ignition switch (not shown). Then, the following steps are repeated at predetermined intervals. As shown, the air/fuel ratio control circuit 32 first detects whether or not the flag $F_A$ is eual to "1" at a step 51.. If $F_A=0$, it means that the first and second sensors are not yet activated. In this state, the control circuit 32 detects as to whether or not the flag $F_H$ is equal to "1" at a step 52. If $F_H=0$, this means that the supply of the heater current is not started, and the control circuit 32 reads the engine cooling water temperature $T_W$ from an output signal of the cooling water temperature sensor 36, at a step 53. Further, the control circuit 32 sets an activation time period $T_{FB}$ for the activation of the sensor, which corresponds to the detected cooling water temperature $T_W$, at a step 54. Various values for the activation time period $T_{FB}$ each corrresponding to values of the cooling water temperature $T_W$ are previously stored in a memory, such as a ROM, in the control circuit 32 in the form of a data map. The relation between the activation time period $T_{FB}$ and the cooling water temperature $T_W$ is as shown in FIG. 8. The setting of the activation time period $T_{FB}$ is performed, at control circuit 32, by searching a value of the activation time period $T_{FB}$ from the data map, using the read value of the cooling water temperature $T_W$. The activation time period $T_{FB}$ is determined in such a manner that it becomes long as the cooling water temperature $T_W$ decreases. After the setting of the activation time period $T_{FB}$, the heater current supply start command is supplied from the control circuit 32 to the heater current supply circuit 35 at a step 55, and the value "1" is set for the heater current supply start flag $F_H$, at a step 56. By the generation of the heater current supply start command, the heater elements 19 and 20 are supplied with the heater current to heat the oxygen concentration sensor 40. Then, the control circuit 32 detects whether or not the activation time period $T_{FB}$ has passed after the generation of the heater current supply start command, at a step 57. When the activation time period $T_{FB}$ has passed after the generation of the heater current supply start command, the value "1" is set for the flag $F_A$ for discriminating the activation of the sensor, at a step 58. If it is detected that the flag $F_H$ is equal to 1 ($F_H=1$) at the step 52, it means that the supply of the heater current is already started. Therefore, the operation of the step 57 is executed immediately.

On the other hand, if it is detected that the flag $F_A$ is equal to 1 ($F_A=1$) at a step 51, it means that the activation of the sensor is completed. Therefore the air/fuel ratio control circuit 32 detects as to which of the first and second sensor should be selected, at a step 59. This determination is performed in response to the engine operation or the controlled state of the air/fuel ratio. If it is determined that the first sensor should be selected, the control circuit 32 supplies a first sensor selection command to the drive circuit 30, at a step 60. Conversely, if it is determined that the second sensor sould be selected, the control circuit 32 supplies a second sensor selection command to the drive circuit 30, at a step 61. In response to the first sensor selection command, the control circuit 30 drives the switches 28a and 28b towards the aforementioned positions for selecting the first sensor. These switch positions are maintained until the second sensor selection command or a selection cancel command is supplied from the control circuit 32. When the first sensor is selected in this way, the pump current is supplied to the first oxygen pump unit 15. Similarly, in response to the second sensor selection command, the control circuit 32 drives the switches 28a and 28b towards the aforementioned positions for selecting the second sensor. These switch positions for selecting the second sensor is maintained until the first sensor selection command or the selection cancel command is supplied from the control circuit 32. When the second sensor is selected in this way, the pump current is supplied to the second pump element 16.

Then, the control circuit 32 reads in a pump current value $I_P(1)$ or a pump current value $I_P(2)$ from the A/D converter 31 at a step 62. Then the control circuit 32 detects as to whether or not an oxygen concentration detection output signal value $L_{O2}$, corresponding to the pump current value $I_P(1)$ or the pump current value read at the step 62, is higher than a reference value $L_{ref}$ which corresponds to a target air/fuel ratio, at a step 63. If $L_{O2} \leq L_{ref}$, it means that the air/fuel ratio of the mixture supplied to the engine is rich. Therefore, the control circuit 32 generates a valve open drive command for opening the solenoid valve 34, and supplies it to the drive circuit 33, at a step 64. If $L_{O2} > L_{ref}$, it means that the air/fuel ratio of the mixture is lean, and a valve open drive stop command for closing the solenoid valve 34 is generated by the control circuit 32 and in turn supplied to the drive circuit 33 at a step 65. In accordance with the valve open drive command, the drive circuit 33 opens the solenoid valve 34 to introduce the secondary air into the intake manifold of the engine, so that the air/fuel ratio of the mixture is made lean. Conversely, in response to the valve open drive stop command, the drive circuit 33 closes the solenoid valve 34, so that the air/fuel ratio of mixture is enriched. By executing these operations repeatedly at predetermined intervals, the air/fuel ratio of the mixture supplied to the engine is controlled to the target air/fuel ratio. In the embodiment of the present invention explained so far, the air/fuel raito of the mixture is controlled to the target air/fuel ratio by controlling the supply of the secondary air in response to the output signals of the first and second sensors. However, the arrangement is not limited to this, and as an example, the air/fuel ratio of the mixture can be controlled by adjusting the amount of fuel in response to the output signals of the first and second sensors.

It will be appreciated from the foregoing, in the method for controlling the oxygen concentration sensor according to the present invention, the supply of the current across the electrodes of the oxygen pump element is started after the elapse of more than a time period after the start of the supply of the heater current, which time period is determined in response to the engine temperature at a time of the start of the supply of the heater current. Therefore, upon cold start of the engine, the open loop control of the air/fuel ratio is selected to enrich the air/fuel ratio until the temperature of the oxygen concentration sensor has risen to a high temperature level on which the desired proportional output signal characteristic of the oxygen concentration sensor is obtained. The driveability of the engine is improved as a result. Further, when the engine is started under a hot condition, the activation of the oxygen concentration sensor completes more sooner than in the case of the cold start, and the supply of the current to the oxygen pump elements starts earlier according as the temperature rises faster. Thus, the purification of the exhaust gas is performed in an improved manner. Moreover, the occurence of the so-called blackening phenomenon is surely prevented because of the supply of the heater current is stopped during the time period determined in response to the engine temperature at the time of the start of the supply of the current to the heater elements, after the start of the supply of the latter current.

What is claimed is:

1. A method for controlling an oxygen concentration sensor mounted on an internal combustion engine having an exhaust gas passage, which sensor includes: a pair of oxygen ion conductive solid electrolyte members with electrodes and disposed in said exhaust gas passage; one of said oxygen io conductive solid electrolyte members being operative as an oxygen pump element, and the other of said oxygen ion conductive solid electrolyte members being operative as a sensor cell element for measuring an oxygen concentration ratio; a pump current source for supplying a pump current to be supplied across said electrodes of said oxygen pump element; and a heater element arranged to heat said oxygen ion conductive solid electrolyte members when a heater current is supplied thereto, said method comprising:
   a detection step for detecting a temperature of the engine immediately before a start of a supply of said heater current; and
   a control step for controlling a supply of said pump current so that the supply of said pump current is started when an elapse of more than a time period determined correspondingly to said temperature of the engine from a time of the supply of said heater current, is detected.

* * * * *